United States Patent [19]

Swallow

[11] 4,051,256

[45] Sept. 27, 1977

[54] GUANIDINE DERIVATIVES

[75] Inventor: Douglas Lintin Swallow, Macclesfield, England

[73] Assignee: Imperial Chemical Industries Limited, London, England

[21] Appl. No.: 706,554

[22] Filed: Aug. 11, 1975

[51] Int. Cl.² ............................................. C07C 129/12
[52] U.S. Cl. .................................. 424/304; 260/294.9; 260/295 G; 260/296 R; 260/465 E; 260/471 R; 260/501.14; 260/565; 424/263; 424/309; 424/316; 424/326
[58] Field of Search ............... 260/565, 465 E, 471 R, 260/501.14; 424/326, 304, 309, 316

[56] References Cited

PUBLICATIONS

Geluk et al., J. Med. Chem. vol. 12, pp. 712–715 (1969).

Primary Examiner—Gerald A. Schwartz

Attorney, Agent, or Firm—Cushman, Darby & Cushman

[57] ABSTRACT

Guanidine derivatives of the formula:

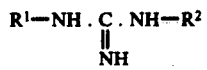

in which $R^1$ is a cyclohexyl, adamantyl, bicycloheptanyl, bicycloheptenyl, tricycloheptanyl or tetracyclononanyl radical and $R^2$ is a phenyl or pyridyl radical optionally substituted by 1 or 2 halogen atoms, or alkyl, cyanoalkyl, alkoxycarbonyl or amino radicals, and the pharmaceutically-acceptable acid-addition salts thereof, active against rhinoviruses, are disclosed, along with processes for their manufacture, compositions containing them, a method of combatting rhinoviral infections and a method of selectively killing rhinoviruses in a mixed virus population.

10 Claims, No Drawings

GUANIDINE DERIVATIVES

This invention relates to new guanidine derivatives which possess antiviral properties.

According to the invention there is provided a guanidine derivative of the formula:

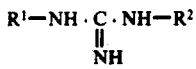

I wherein $R^1$ is a cyclohexyl, adamantyl, bicyclo[2,2,1]-heptanyl, bicyclo[2,2,1]hept-5-enyl, tricyclo[2,2,1,0$^{2,6}$]-heptanyl or tetracyclo[4,3,0,0$^{2,4}$,0$^{3,7}$]nonanyl radical and $R^2$ is a phenyl or pyridyl radical optionally substituted by 1 or 2 substituents selected from halogen atoms, alkyl and cyanoalkyl radicals of 1 to 6 carbon atoms, alkoxycarbonyl radicals of 2 to 6 carbon atoms and amino radicals; and the pharmaceutically-acceptable acid-addition salts thereof.

The formulae in 3-dimensional representation for adamantyl (II), bicyclo[2,2,1]heptanyl (III), bicyclo[2,2,1]-hept-5-enyl (IV), tricyclo[2,2,1,0$^{2,6}$]heptanyl (V) and tetracyclo[4,3,0,0$^{2,4}$,0$^{3,7}$]nonanyl (VI) radicals are as follows:

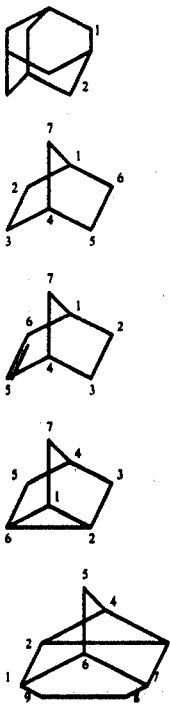

The point of attachment in radicals II, III, IV, V or VI may be at any of the numbered positions shown, some of which are identical to each other, and may be in any one of the possible stereochemical configurations. For example in positions 2, 3, 5 or 6 in formula III, positions 5 or 6 in formula IV, positions 3 or 5 in formula V and positions 8 or 9 in formula VI, the linkage may have either the exo or endo configuration, that is it may be cis or trans respectively with respect to the bridge position (7 in formulae III, IV and V and 5 in formula VI).

It will be observed that when $R^1$ is a bicyclo[2,2,1]-heptanyl, bicyclo[2,2,1]hept-5-enyl, tricyclo[2,2,1,0$^{2,6}$]-heptanyl or tetracyclo[4,3,0,0$^{2,4}$,0$^{3,7}$]nonanyl radical and the molecule does not contain a plane of symmetry, the guanidine derivative of the invention will contain an optically-active centre and may therefore be resolved into two optically-enantiomeric forms. It is to be understood that in such cases, this invention encompasses the racemic form and both optically-active enantiomers of such a derivative.

Particular groups of compounds of the invention within the above definition are as follows:

Those wherein $R^1$ is an adamantyl, bicyclo[2,2,1]-heptanyl, bicyclo[2,2,1]hept-5enyl or tricyclo[2,2,1,0$^{2,6}$]-heptanyl radical.

Those wherein $R^1$ is a cyclohexyl, adamant-1-yl, exo-bicyclo[2,2,1]heptan-2-yl, endo-bicyclo[2,2,1]heptan-2-yl, exo-bicyclo[2,2,1]hept-5-en-2-yl, tricyclo[2,2,1,0$^{2,6}$]heptan-3-yl or tetracyclo[4,3,0,0$^{2,4}$,0$^{3,7}$]nonan-8-yl radical and $R^2$ is a pyridyl radical or a phenyl radical optionally substituted by 1 or 2 fluorine atoms, by a chlorine or bromine atom, or by a methyl, cyanomethyl, methoxycarbonyl or amino radical.

Those in which $R^1$ is in the exo-configuration.

Those in which $R^2$ carries one optional substituent.

Those in which $R^1$ is an exo-bicyclo[2,2,1]hept-5-en-2-yl or exo-bicyclo[2,2,1]heptan-2-yl radical and $R^2$ is an optionally substituted phenyl radical.

Those in which $R^1$ is an exo-bicyclo[2,2,1]hept-5-en-2-yl radical and $R^2$ is a phenyl radical bearing a single optional substituent which, for example, may be in the 4-position and may, for example, be a fluorine, chlorine or bromine atom.

Particular compounds of the invention are described in the Examples and of those a preferred compound is 2-exo-[3-(p-chlorophenyl)guanidino]bicyclo[2,2,1]hept-5-ene and the pharmaceutically-acceptable acid-addition salts thereof.

A suitable pharmaceutically-acceptable acid-addition salt of the guanidine derivative of the invention is, for example, a hydrochloride, phosphate or sulphate or a citrate, acetate, succinate or fumarate.

The guanidine derivative of the invention may be manufactured by methods known in themselves for the manufacture of chemically analogous compounds, for example:

a. reaction of a thiourea of the formula:

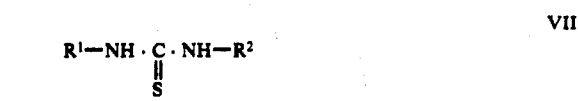

VII or a thiouronium salt thereof, with ammonia in the presence of a catalyst;

b. reaction of a cyanamide of the formula $R^1$—NHCN or $R^2$—NHCN with an amine of the formula $R^2$—NH$_2$ or $R^1$—NH$_2$ respectively;

c. reaction of a carbodi-imide of the formula:

VIII with ammonia; or d. for those compounds in which $R^1$ is a cyclohexyl or bicyclo-[2,2,1]heptanyl radical, reducing a compound of the formula:

IX

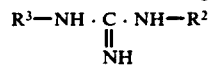

in which R³ is cyclohexenyl or bicyclo[2,2,1]heptenyl radical; and e. for a compound which is an optically-active enantiomer, resolution of the racemic compound of the formula I given above by conventional means, or by use of any of processes (a) to (d) above in which the starting material is itself a resolved isomer.

Process (a) is preferably carried out in a diluent or solvent such as ethanol. A preferred catalyst for use in the process is a heavy metal oxide, for example yellow mercuric oxide or lead oxide, and the reaction is preferably conducted at a temperature between 0° C. and 100° C. or the boiling point of the diluent or solvent, whichever is the lower. Use of a temperature above room temperature may require constant addition of ammonia in the form of a gas stream. The thiouronium salt used as an optional starting material may have the formula:

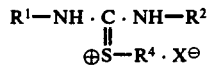

in which R⁴ is an alkyl radical of 1 to 4 carbon atoms, for example a methyl radical and X⊖ is an anion, for example a halide anion such as a chloride, bromide or iodide anion.

Process (b) may be carried out in the presence or absence of a diluent or solvent at a temperature of between 50° and 250° C., the upper limit being restricted to the boiling point of the optional diluent or solvent. A suitable optional diluent or solvent is, for example, n-butanol. The amine component in the reaction is preferably used in the form of a salt, for example a hydrochloride.

Process (c) may be conducted under the same conditions as process (a), though of course no catalyst is necessary.

Process (d) may be carried out using hydrogen in a diluent or solvent, for example ethanol, in the presence of a catalyst, for example a palladium-on-charcoal catalyst, for example a 5% w/w palladium-on-charcoal catalyst. The hydrogen may be at atmospheric pressure or at a pressure of up to 5 atmospheres.

The resolution in process (e) may be accomplished, for example, by fractional crystallisation of a salt of the racemic derivative of the formula I with an optically-active acid, for example (+)- or (−)- mandelic acid or (+)-O,O-dibenzoyltartaric acid.

The starting material of the formula VII for use in process (a) may be obtained by reaction of an amine of the formula R²—NH₂ or R¹—NH₂ with an isothiocyanate of the formula R¹—NCS or R²—NCS respectively. The isothiocyanate itself may be obtained by reaction of an amine of the formula R¹—NH₂ or R²—NH₂ with thiophosgene.

The starting material of the formula R¹—NHCN for use in process (b) may be obtained by reaction of a compound of the formula R¹—NCS with ammonia to give the thiourea

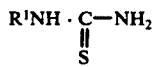

which is then reacted with yellow mercuric oxide to give the required product; or by reaction of an amine of formula R¹—NH₂ with cyanogen bromide.

The starting material of the formula VIII for use in process (c) may be obtained by reaction of the compound of the formula VII with triphenylphosphine in the presence of carbon tetrachloride and triethylamine.

The new compounds of the invention possess antiviral activity, and in particular they are specifically active against rhinoviruses which, for example, inhabit and multiply in the upper respiratory tract of warm blooded animals including man. This activity is demonstrated by a tissue culture assay in human embryo lung cells whereby it may be shown that the compounds inhibit the growth of at least 16 different rhinoviruses at a concentration which produces no morphological abnormalities on the tissue culture cells. All the compounds exemplified in this specification are 50% active against rhinovirus type 2 at or below a concentration of 5 μg./ml. whilst producing no morphological abnormalities in confluent monolayers of tissue culture cells at a concentration of at least four times the active dose. Thus, for example, the compound of the invention 2-exo-[3-(p-fluorophenyl)guanidino]bicyclo[2,2,1]hept-5-ene is 50% active against rhinovirus type 2 at a concentration of 0.02 μg./ml. while it causes 50% of the cells in the tissue culture sheet to show abnormalities only at a concentration of 25 μg./ml., a therapeutic ratio of 1250.

The compound of the invention may be incorporated as active ingredient into a pharmaceutical composition for the purpose of treating a rhinovirus infection in warm blooded animals. Owing to the highly selective nature of its antiviral spectrum, the compound of the invention may also be used in diagnostic studies and in public health laboratories selectively to inhibit the growth of rhinoviruses whilst allowing other viruses such as the enteroviruses, the arborviruses, myxoviruses, and DNA-containing viruses, against which the compound of the invention has no effect, to multiply normally in tissue culture.

When used in warm blooded animals to produce the desired effect, a daily oral dose of from 1 mg./kg. to 15 mg./kg. of a compound of the invention is desirable. When used in man this is equivalent to a daily dose of between 70 mg. and 1 g. In man a daily dose of between 70 mg. and 250 mg. given in divided doses, is preferred. In man a daily nasal dose of 1 to 125 μg., and preferably 1 to 25 μg., is desirable.

The compound of the invention may be used in the form of a pharmaceutical composition which comprises as active ingredient a guanidine derivative of the invention in association with a pharmaceutically-acceptable diluent or carrier therefor.

The pharmaceutical composition of the invention may be in the form of a conventional tablet, lozenge, capsule, aqueous or oily solution or suspension, emulsion, nasal drops, spray, aerosol (either wet, or dry powder) or snuff, and may be manufactured by conventional techniques and incorporate conventional excipients.

Preferred compositions of the invention are those which produce a virucidal level of the guanidine derivative of the invention in those parts of the body where rhinoviruses normally grow, for example the mucosa of the nose, throat, mouth and bronchi, either by direct application of the composition to those parts or indirectly by producing a sufficient blood-level of the guanidine derivative after oral dosing.

Such preferred compositions for direct application are, for example, lozenges which may be dissolved slowly in the mouth, in order to bathe the mouth and associated passages with a solution of the active ingredient, nasal sprays or wet aerosols in the form of a solution or suspension of the guanidine derivative in an inert pharmaceutically-acceptable liquid, or a dry powder aerosol which contains a guanidine derivative of the invention in finely powdered form, any of which may be inhaled and deposited in the nasal and bronchial passages, and preferred compositions for oral dosage are, for example, tablets.

A suitable tablet or lozenge contains from 25 mg. to 100 mg. of an antiviral compound of the invention, and the normal regimen for the prophylaxis or treatment of a rhinoviral infection is one tablet two to four times per day.

A suitable nasal spray or aerosol contains from 5 μg. to 50 μg. of an antiviral compound of the invention per ml. of solution or suspension and for the prophylaxis or treatment of a rhinoviral infection about 0.1 ml. of such a solution is sprayed into the nose by the subject three to six times per day.

The compositions of the invention may also contain other known pharmaceutically useful compounds, for example nasal decongestants, antipyretics or antiseptics. Owing to the highly selective nature of its antiviral spectrum, the compound of the invention is also useful in hospital and public health laboratories for selectively inhibiting rhinorvirus growth in tissue cultures, thus allowing other viruses which may be present to be detected more easily. For example, clinical specimens from patents with upper respiratory tract disease may be cultured in the presence of a compound of the invention. Rhinoviruses grow in the upper respiratory tract of man, and rhinoviruses will often be present in such specimens. Rhinovirus growth during incubation is prevented but other viruses which may be present, such as influenza, adenoviruses and respiratory syncytial virus, grow unchecked. Similarly, in the public health field, the growth of rhiniviruses may be suppressed while other viruses such as the enteroviruses, the arborviruses, myxoviruses, and DNA-containing viruses, against which the compounds of the invention have no effect, continue to multiply normally in tissue culture.

As a further alternative, the ability of the compound of the invention selectively to inhibit the growth of rhinoviruses in the presence of other viruses provide a diagnostic tool for the speedy identification of rhinoviruses in a mixed virus population.

In use the compound of the invention is added as a suspension or solution in a suitable diluent or solvent, which is generally water or the tissue culture medium, to the tissue culture under examination. The final concentration of the compound of the invention may be varied over a wide range, but is generally in the range of 0.04 to 45 μg./ml. The culture is then incubated for the appropriate period of time at the appropriate temperature before examination for viral growth.

For example, human embryonic lung cells growing in Eagle's medium in 4 × ½ inch glass tubes were doubly infected with 100 TCD$_{50}$ of herpes simplex type 1 virus and 100 TCD$_{50}$ of rhinoviruses type 2 and incubated at 33° C. Two days later, the cells were seen to be degenerating due to the growth of the viruses and the culture fields were shown by infectivity titrations to contain at least a hundred times more of each virus than the original inoculum.

In a parallel experiment the culture medium was prepared containing 2-exo-[3-(p-chlorophenyl)guanidino]-bicyclo-[2,2,1]hept-5-ene at a concentration of 2.5 μg./ml. This medium was added to doubly infected cell cultures which were incubated at 33° C. for two days, as above. The cells were then again seen to be degenerating due to virus growth, but the culture fluids were shown to contain a high concentration of herpesvirus only, the growth of rhinovirus having been suppressed.

The invention is illustrated, but not limited, by the following Examples in which the temperatures are in degrees Centigrade.

EXAMPLE 1

A solution of 2-exo-[3-(p-fluorophenyl)thioureido]-bicyclo[2,2,1]hept-5-ene (2 g.) in saturated ethanolic ammonia (60 ml.) was stirred at room temperature with yellow mercuric oxide (1.74 g.) for 16 hours. The reaction mixture was boiled on a steam bath for 15 minutes to drive off excess ammonia and to congulate the fine precipitate of mercuric sulphide. This solid was filtered off, washed with boiling ethanol (10 ml.) twice, and the combined filtrates evaporated to dryness. The solid residue was recrystallised from ethyl acetate to give 2-exo-[3-(p-fluorophenyl)guanidino]bicyclo-[2,2,1]hept-5-ene, m.p. 192°-194° C.

The 2-exo-[3-(p-fluorophenyl)thioureido]bicyclo-[2,2,1]hept-5-ene used as starting material may be prepared as follows:

A solution of p-fluoroaniline (2.6 g.) in 25 ml. chloroform was added to 2-exo-isothiocyanatobicyclo[2,2,1]-hept-5-ene (3.0 g.) and the mixture stirred at room temperature for 16 hours. The mixture was then heated under reflux for 5 hours to complete the reaction, cooled, and the solid product filtered off, washed with a little cold chloroform and dried. Recrystallisation from toluene gave 2-exo-[3-(p-fluorophenyl)thioureido]bicyclo[2,2,1]hept-5-ene, m.p. 201°-203° C.

EXAMPLE 2

The process described in Example 1 was repeated using appropriately substituted starting materials and the following compounds were obtained:

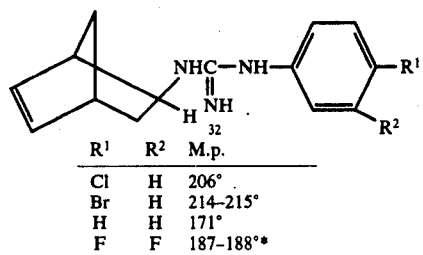

| R$^1$ | R$^2$ | M.p. |
|---|---|---|
| Cl | H | 206° |
| Br | H | 214-215° |
| H | H | 171° |
| F | F | 187-188°* |

*Recrystallised from toluene

The starting materials for the above process were obtained by repeating the process described in the second part of Example 1 using the appropriately substituted aniline in place of p-fluoroaniline as starting material, and cyclohexane in place of chloroform as solvent, and the following compounds were obtained:

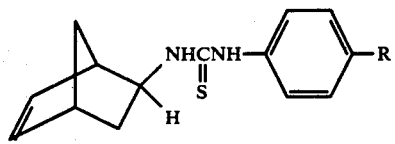

| R | M.p. |
|---|---|
| Cl | 183° |
| Br | 145° |
| H | 164° |

EXAMPLE 3

A solution of 2-exo-[3-(p-fluorophenyl)guanidino]bicyclo[2,2,1]hept-5-ene (0.5 g.) in ethanol (25 ml.) was hydrogenated at room temperature and pressure in the presence of 5% w/w palladium-on-charcoal (0.05 g.) until no more hydrogen was taken up. The mixture was filtered and the solvent evaporated in vacuo. The residual solid was recrystallised from ethyl acetate to give 2-exo-[3-(p-fluorophenyl)guanidino]bicyclo[2,2,1]heptane, m.p. 186°.

EXAMPLE 4

The process described in Example 3 was repeated using the appropriately substituted starting materials and the following compounds were obtained:

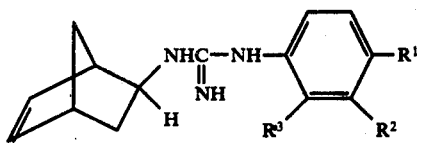

| $R^1$ | $R^2$ | M.p. |
|---|---|---|
| Cl | H | 204° |
| F | F | 177° |

EXAMPLE 5

A solution of 1-(p-fluorophenyl)-3-(2-exo-bicyclo[2,2,1]hept-5-enyl)carbodiimide (0.9 g.) in saturated ethanolic ammonia (10 ml.) was allowed to stand at room temperature for 48 hours. The solvent was evaporated in vacuo from the suspension, and the residual solid was crystallised from ethyl acetate to give 2-exo-[3-(p-fluorophenyl)guanidino[bicyclo[2,2,1]hept-5-ene, m.p. 194°.

The 1-(p-fluorophenyl)-3-(2-exo-bicyclo[2,2,1]hept-5-enyl)carbodiimide used as starting material was obtained as follows:

To a solution of 2-exo-[3-(p-fluorophenyl)thioureido]bicyclo[2,2,1]hept-5-ene (1.55 g.) in dry methylene chloride (6 ml.) were added carbon tetrachloride (0.9 g.), triethylamine (0.58 g.) and triphenyl phosphine (1.8 g.). The mixture was heated to 40°. After 20 minutes a clear solution had formed. After a further 1.5 hours at 40° the solution was cooled. The solvent was removed by evaporation and the residue extracted with cold petroleum ether (b.p. 60°-80°; 3 × 10 ml.). On evaporation of the extract, the required 1-(p-fluorophenyl)-3-(2-exo-bicyclo[2,2,1]hept-5-enyl)carbodiimide was obtained as a yellow oil, identified by mass spectrometry (Mass ion 228) and infra-red spectrometry (N=C=N very strong absorption at 2100 cm$^{-1}$), and was used without further purification.

EXAMPLE 6

The process described in Example 1 was repeated using 1-(3-p-chlorophenylthioureido)adamantane as starting material and there was thus obtained 1-[3-(p-chlorophenyl)-guanidino]adamantane, m.p. 196°.

The 1-[3-(p-chlorophenyl)thioureido]adamantane used as starting material was obtained as follows:

Separate solutions of 1-aminoadamantane (0.9 g.) and p-chlorophenylisothiocyanate (0.9 g.) in chloroform (10 ml.) were mixed and stirred at 20° for 3 days. The solvent was evaporated in vacuo and the residual solid recrystallised from toluene to give 1-[3-(p-chlorophenyl)-thioureido]adamantane, m.p. 185°.

EXAMPLE 7

The process described in Example 1 was repeated using appropriately substituted starting materials and the following compounds were obtained:

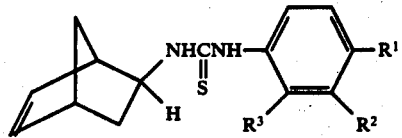

| $R^1$ | $R^2$ | $R^3$ | m.p. | Footnote |
|---|---|---|---|---|
| H | Cl | H | 154 | 1 |
| CH$_3$ | H | H | 208-209 | 1 |
| H | CH$_3$ | H | 179-181 | 2 |
| H | H | CH$_3$ | 160-162 | 2 |
| CH$_2$CN | H | H | 170 | 1 |
| COOCH$_3$ | H | H | 199-200 | 1 |
| NH$_2$ | H | H | 204-205 | 3 |
| H | NH$_2$ | H | 158-160 | 2 |

Footnotes
1. Recrystallised from ethyl acetate
2. Recrystallised from toluene
3. Hydrochloride, recrystallised from isopropanol/ethyl acetate The starting materials for the above process were obtained by repeating the process described in the second part of Example 1 using the appropriately-substituted aniline as starting material in place of p-fluoroaniline, and cyclohexane in place of chloroform as solvent, and the following compounds were obtained:

| $R^1$ | $R^2$ | $R^3$ | m.p. | Footnote |
|---|---|---|---|---|
| H | Cl | H | 140-141 | 1 |
| CH$_3$ | H | H | 173 | 1 |
| H | CH$_3$ | H | 125-128 | 2 |
| H | H | CH$_3$ | 174-175 | 3 |
| COOCH$_3$ | H | H | 177-178 | 3 |
| NH$_2$ | H | H | 158 | 1 |
| H | NH$_2$ | H | — | 4 |

Footnotes
1. Recrystallised from toluene
2. Recrystallised from ether
3. Recrystallised from ethyl acetate
4. Used without further purification

EXAMPLE 8

The process described in Example 1 was repeated using 2-exo-[3-(4-pyridyl)thioureido]bicyclo[2,2,1]hept-5-ene hydrochloride in place of the 2-exo-[3-(p-fluorophenyl)thioureido]-bicyclo[2,2,1]hept-5-ene. There was thus obtained 2-exo-[3-(4-pyridyl)guanidino]bicyclo[2,2,1]hept-5-ene which was converted to its dihydrochloride salt and recrystallised from a mixture of ethanol and ethyl acetate, giving a product melting at 282° with decomposition.

The starting material was obtained by repeating the process described in the second part of Example 1 using 4-aminopyridine in place of p-fluoroaniline and refluxing for 3 days instead of 5 hours. The product was isolated at its hydrochloride salt and had a melting point of 200°–201°.

EXAMPLE 9

The process of Example 1 was repeated using 2-endo-(3-phenylthioureido)bicyclo[2,2,1]heptane as starting material in place of 2-exo-[3-(p-fluorophenyl)thioureido]bicyclo[2,2,1]-hept-5-ene. There was thus obtained 2-endo-(3-phenylguanidino)-bicyclo[2,2,1]heptane, m.p. 132°–133° on recrystallisation from toluene.

The starting material may be prepared as follows:

A solution of 2-endo-aminonorbornane in cyclohexane (obtained by extraction of an alkaline solution in water of 2-endo-aminonorbornane hydrobromide (1.5 g.) with cyclohexane followed by drying over anhydrous magnesium sulphate), was added to a solution of phenylisothiocyanate (1.38 g.) in cyclohexane and stirred for 10 hours at room temperature. The precipitated produced was filtered off, washed with cyclohexane and then recrystallised from cyclohexane to give 2-endo-(3-phenylthioureido)bicyclo[2,2,1]heptane, m.p. 154°.

EXAMPLE 10

1-Cyclohexyl-3-(p-chlorophenyl)thiourea (2.0 g.) was dissolved in absolute ethyl alcohol saturated with ammonia (40 ml.). To this was added yellow mercuric oxide (1.7 g.) and the mixture stirred at room temperature for 16 hours. The mixture was then refluxed 15 minutes to coagulate the fine precipitate of mercuric sulphide, filtered and the clear filtrate evaporated to dryness. The residue was recrystallised from toluene to give 1-cyclohexyl-3-(p-chlorophenyl)guanidine, m.p. 187°–190°.

The starting material may be obtained as follows:

To a solution of cyclohexylamine (1.75 g.) in chloroform (15 ml.) was added dropwise with stirring a solution of p-chlorophenylisothiocyanate (3.0 g.) in chloroform (15 ml.) at room temperature. After stirring 3 hours, the white solid was filtered off, washed with a little CHCl$_3$ and recrystallised from toluene to give 1-cyclohexyl-3-(p-chlorophenyl)thiourea, m.p. 179°–180°.

EXAMPLE 11

To a solution of 3-[3-(p-chlorophenyl)thioureido]-tricyclo[2,2,1,0$^{2,6}$]heptane (0.25 g.) in ethanol saturated with ammonia (10 ml.) was added 0.2 g. of yellow mercuric oxide, and the mixture stirred at room temperature for 16 hours. The solids were filtered off and the clear filtrate evaporated to dryness. The residual solid was recrystallised from toluene to give 3-[3-(p-chlorphenyl)guanidino]tricyclo[2,2,1,0$^{2,6}$]heptane, m.p. 204°–205°.

The thiourea used as starting material may be prepared as follows:

3-Aminotricyclo[2,2,1,0$^{2,6}$]heptane (21 g.) (prepared as described in U.K. Patent Specification No. 1,051,319), was dissolved in chloroform (25 ml.) and added slowly, below 10°, to a stirred solution of thiophosgene (22 g.) in chloroform (20 ml.). When addition was complete the mixture was allowed to attain ambient temperature and stirred a further 2 hours. The chloroform solution was consecutively washed with 20 ml. portions of water, 1N NaOH, and water again, dried over anhydrous MgSO$_4$, filtered and the chloroform evaporated in vacuo. The residual oil was fractionally distilled in vacuo to give 3-isothiocyanatotricyclo[2,2,1,0$^{2,6}$]heptane, b.p. 70°–76° at 0.4 mm. Hg. pressure.

This isothiocyanate (1.2 g.) was dissolved in chloroform (30 ml.) and to it was added p-chloroaniline (2.1 g.). The latter rapidly dissolved and the mixture was refluxed for 3 hours. The cooled solution was extracted with aqueous 2N HCl (10 ml.), washed with water (10 ml.) and dried over anhydrous MgSO4. After filtration, the solvent was evaporated in vacuo and the solid residue recrystallised from toluene to give 3-[3-(p-chlorophenyl)thioureido]tricyclo[2,2,1,0$^{2,6}$]heptane, m.p. 164°–166°.

EXAMPLE 12

8-[3-(p-Chlorophenyl)thioureido]tetracyclo[4,3,0,0$^{2,4}$,0$^{3,7}$]nonane (0.30 g.) was dissolved in ethanol saturated with ammonia (100 ml.) at room temperature and stirred with yellow mercuric oxide (0.43 g.) for 6 hours. The mixture was then boiled for 15 minutes to remove excess ammonia, filtered and the filtrate evaporated to dryness. The solid residue was recrystallised from toluene/cyclohexane (1:2 v/v) to give 8-[3-(p-chlorophenyl)guanidino]tetracyclo[4,3,0,0$^{2,4}$,0$^{3,7}$]nonane, m.p. 170°–171°.

The thiourea used as starting material may be prepared as follows:-

8-Aminotetracyclo[4,3,0,0$^{2,4}$,0$^{3,7}$]nonane hydrochloride (0.5 g.) (prepared as described in U.K. Patent Specification No. 1,180,749) was dissolved in a mixture of chloroform (25 ml.) and triethylamine (0.33 g.). To this solution was added p-chlorophenylisothiocyanate (0.5 g.) and the mixture refluxed for 16 hours. The chloroform solution, after cooling, was washed successively with 10 ml. portions of 2N HCl, water and saturated brine, and then dried over anhydrous MgSO4. After filtration, the solvent was evaporated in vacuo and the residue crystallised from toluene/cyclohexane (1:2 v/v) to give 8-[3-(p-chlorophenyl)thioureido]tetracyclo[4,3,0,0$^{2,4}$,0$^{3,7}$]-nonane, m.p. 168°–170°.

EXAMPLE 13

2-Endo-aminobicyclo[2,2,1]heptane hydrobromide (0.96 g.) was intimately mixed with p-chlorophenylcyanamide (0.76 g.) and heated at 200°–220° for 15 minutes. The mixture quickly liquefied and was stirred occasionally. It was allowed to cool and then treated with ethyl acetate (10 ml.) and water (5 ml.) which dissolved the residue. The organic phase was extracted three times with 5 ml. amounts of water. The aqueous phases were combined and basified with aqueous 10N NaOH. The precipitated solid was filtered off, washed with water, dried and shown by t.l.c. to be pure quanidine. The ethyl acetate layer was shown by t.l.c. still to contain the required guanidine. It was therefore extracted with 2N NaOH (3 × 5 ml.), dried over anhydrous $K_2CO_3$, filtered and evaporated and the residue recrystallised from toluene to give 2-endo-[3-(p-chlorophenyl)guanidino]bicyclo[2,2,1]heptane, m.p. 179°-181°.

EXAMPLE 14 p-Chloroaniline hydrochloride (1.25 g.) was dissolved in n-butanol (10 ml.) and heated to reflux. A cold solution of 2-exo-cyanamidobicyclo[2,2,1]hept-5-ene (1.07 g.) in butanol (10 ml.) was added slowly dropwise so that the mixture continued to reflux. One hour after the addition was complete the mixture was cooled, butanol evaporated off in vacuo and the residue dissolved in ethyl acetate (10 ml.). The organic phase was extracted with water (4 × 5 ml.). The combined aqueous phases were brought to pH7 with aqueous $Na_2CO_3$ solution and extracted with ether. This removed unreacted p-chloroaniline. The residual aqueous phase was brought to pH 12 with aqueous 10N NaOH which precipitated pure product. It was filtered off, washed with water, dried and recrystallised from ethyl acetate to give 2-exo-[3-(p-chlorophenyl)guanidino]bicyclo[2,2,1]hept-5-ene, m.p. 206°-207°.

The 2-exo-cyanamidobicyclo[2,2,1]hept-5-ene used as starting material may be obtained as follows:

2-Exo-isothiocyanatobicyclo[2,2,1]hept-5-ene (50 g.) was dissolved in ethanol (200 ml.) and concentrated aqueous ammonia (S.G. 0.88, 10 ml.) added. This mixture was refluxed and a further (50 ml.) of concentrated aqueous ammonia added dropwise over 30 minutes. After 3 hours total reflux, the solution was cooled and the required product crystallised out, to give 2-exo-thioureidobicyclo[2,2,1]hept-5-ene (50.35 g.), m.p. 158°-159.5°.

This thiourea (1.0 g.) was dissolved in absolute ethanol (50 ml.) at room temperature and freshly prepared yellow mercuric oxide (1.29 g.) added. The mixture was stirred for 24 hours at room temperature and a further portion of HgO (1.29 g.) added. After a further 48 hours stirring the solids were filtered off and washed well with ethanol. The filtrate was taken to dryness in a rotary evaporator keeping the temperature as low as possible. The 2-exo-cyanamidobicyclo-[2,2,1]hept-5-ene thus obtained as a very pale brown gum was dissolved in cold n-butanol (10 ml.) and used immediately.

EXAMPLE 15

2-Exo-[3-(p-chlorophenyl)thioureido]bicyclo[2,2,1]-hept-5-ene (0.5 g.) was dissolved in ethanol (10 ml.) and iodomethane (0.255 g.) added. The mixture was refluxed for 3 hours, during which time the thiourea was converted completely to the S-methylthiouronium iodide. The mixture was cooled and then saturated with ammonia gas. The mixture was refluxed with a constant stream of ammonia passing through for 10 hours, cooled to room temperature, saturated again with ammonia and left to stand for 3 days.

The solvent was evaporated off and the residue taken up in ethyl acetate (10 ml.). An insoluble portion (ammonium iodide) was filtered off and the organic phase extracted with water (4 × 10 ml.). The combined aqueous extracts were basified with 10N NaOH and the precipitate filtered off, washed with water and dried. After recrystallisation from ethyl acetate there was obtained 2-exo-[3-(p-chlorophenyl)guanidino]bicyclo-[2,2,1]hept-5-ene, m.p. 202°-203°.

EXAMPLE 16

A solution of 2-exo-[3-(p-chlorophenyl)guanidino]-bicyclo[2,2,1]hept-5-ene (6.1 g.) in hot ethanol (75 ml.) was stirred while a solution of (+)- mandelic acid (3.54 g.) in hot ethanol (25 ml.) was added dropwise. The mixture was allowed to cool slowly over 16 hours when the precipitate was filtered off, then stirred with a 10 ml. portion of ethanol and refiltered. The two filtrates were combined and retained. The solid filtered off was recrystallised 3 times from ethanol, and then had m.p. 159°-162°. This solid was stirred with 2N NaOH (20 ml.) for 15 minutes, giving the free base of the resolved guanidine, which was filtered off, washed with water (10 ml.) and dried. The solid was recrystallised from ethyl acetate giving (+)-2-exo-[3-(p-chlorophenyl)-guanidino]bicyclo[2,2,1]-hept-5-ene, m.p. 205°-207°, $[\alpha]_D^{21} = +73°$ (c, 1.0 in methanol).

The retained filtrates from the (+)- mandelate salt were evaporated to dryness in vacuo and the base liberated by stirring with cold 2N NaOH (20 ml.). The base was filtered off, washed with water and dried giving 3.0 g. of solid. This was dissolved in hot ethanol (45 ml.) and a solution of (−)- mandelic acid (1.75 g.) in hot ethanol (20 ml.) added. The mixed solutions were allowed to cool slowly over 16 hours. The precipitate was filtered off, washed with ethanol (10 ml.) and then recrystallised twice from ethanol, giving a salt with m.p. 159.5°-162°.

The free base was liberated as above, and after one crystallisation from ethyl acetate gave (−)-2-exo-[3-(p-chlorophenyl)guanidino]bicyclo[2,2,1]hept-5-ene, m.p. 205°-207°, $[\alpha]_D^{21} = -73°$ (c, 1.0 in methanol).

What we claim is:
1. A compound of the formula:

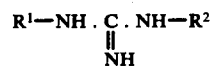

wherein $R^1$ is selected from the group consisting of adamantyl, bicyclo[2,2,1]heptanyl, bicyclo[2,2,1]hept-5-enyl, tricyclo[2,2,1,0$^{2,6}$]heptanyl and tetracyclo[4,3,0,0$^{2,4}$,0$^{3,7}$]-nonanyl and $R^2$ is selected from the group consisting of phenyl optionally substituted by a substituent selected from the group consisting of halogen, alkyl and cyanoalkyl of 1 to 6 carbons, alkoxycarbonyl of 2 to 6 carbons and amino, and the pharmaceutically-acceptable acid-addition salts thereof.

2. The compound of claim 1 wherein $R^1$ is selected from the group consisting of adamant-1-yl, exo-bicyclo[2,2,1]heptan-2-yl, endo-bicyclo[2,2,1]heptan-2-yl, exo-bicyclo[2,2,1]hept-5-en-2-yl, tricyclo[2,2,1,0$^{2,6}$]heptan-3-yl and tetracyclo[4,3,0,0$^{2,4}$,0$^{3,7}$]nonan-8-yl and $R^2$ is selected from the group consisting of phenyl optionally substituted selected from chlorine, bromine, methyl, cyanomethyl, methoxycarbonyl, amino and 1 or 2 fluorines.

3. The compound of claim 1 wherein $R^1$ is in the exo-configuration and $R^2$ carries a single optional substituent.

4. The compound of claim 1 wherein $R^1$ is selected from the group consisting of exo-bicyclo[2,2,1]hept-5-en-2-yl and exo-bicyclo[2,2,1]heptan-2-yl and $R^2$ is a phenyl radical which bears a single optional substituent.

5. The compound of claim 1 wherein $R^1$ is exo-bicyclo[2,2,1]hept-5-en-2-yl and $R^2$ is a phenyl radical which bears a single optional substituent in the 4-position.

6. The compound of claim 5 wherein the single optional substituent in $R^2$ is selected from fluorine, chlorine and bromine.

7. 2-Exo-[3-(p-chlorophenyl)guanidino]bicyclo[2,2,1]hept-5-ene and the pharmaceutically-acceptable acid-addition salts thereof.

8. 2-Exo-[3-(p-fluorophenyl)guanidino]bicyclo[2,2,1]hept-5-ene and the pharmaceutically-acceptable acid-addition salts thereof.

9. A pharmaceutical composition for combatting or preventing a rhinoviral infection in man comprising an effective amount of the compound of claim 1 together with a pharmaceutically-acceptable carrier.

10. A method of combatting or preventing a rhinoviral infection in man which comprises administering an anti-rhinovirally-effective amount of the compound of claim 1.

* * * * *

UNITED STATES PATENT OFFICE
CERTIFICATE OF CORRECTION

Patent No. 4,051,256          Dated September 27, 1977

Inventor(s) Douglas Lintin Swallow

It is certified that error appears in the above-identified patent and that said Letters Patent are hereby corrected as shown below:

In Item [22] the filing date of the application should be --July 19, 1976--

Column 12, line 59 (claim 2) after "substituted"

insert --by a substituent--

Signed and Sealed this

Seventeenth Day of January 1978

[SEAL]

Attest:

RUTH C. MASON          LUTRELLE F. PARKER
*Attesting Officer*          *Acting Commissioner of Patents and Trademarks*